United States Patent
Bastin et al.

(10) Patent No.: US 10,376,484 B2
(45) Date of Patent: Aug. 13, 2019

(54) COMBINATION OF BEZAFIBRATE AND OF RESVERATROL OR RESVERATROL DERIVATIVES FOR THE TREATMENT AND PREVENTION OF DISEASES INVOLVING A MITOCHONDRIAL ENERGY DYSFUNCTION

(71) Applicants: Institut National De La Santé Et De La Recherche Médicale (INSERM), Paris (FR); Universite Paris Descartes, Paris (FR)

(72) Inventors: Jean Bastin, Vitry sur Seine (FR); Fatima Djouadi, Vitry sur Seine (FR)

(73) Assignees: Institut National de la Santé et de la Recherche Médicale (INSERM), Paris (FR); Universite Paris Descartes, Paris (FR)

( * ) Notice: Subject to any disclaimer, the term of this patent is extended or adjusted under 35 U.S.C. 154(b) by 47 days.

(21) Appl. No.: 15/105,116

(22) PCT Filed: Dec. 19, 2014

(86) PCT No.: PCT/EP2014/078910
§ 371 (c)(1),
(2) Date: Jun. 16, 2016

(87) PCT Pub. No.: WO2015/092043
PCT Pub. Date: Jun. 25, 2015

(65) Prior Publication Data
US 2016/0317483 A1 Nov. 3, 2016

(30) Foreign Application Priority Data
Dec. 19, 2013 (FR) .................................. 13 63027

(51) Int. Cl.
A61K 31/05 (2006.01)
A61K 31/195 (2006.01)
A61K 31/7034 (2006.01)

(52) U.S. Cl.
CPC ............ A61K 31/195 (2013.01); A61K 31/05 (2013.01); A61K 31/7034 (2013.01)

(58) Field of Classification Search
CPC ... A61K 31/195; A61K 31/7034; A61K 31/05
See application file for complete search history.

(56) References Cited

U.S. PATENT DOCUMENTS

2009/0054450 A1 * 2/2009 Currie .................. C07C 69/712
514/252.19

FOREIGN PATENT DOCUMENTS

| KR | 10-2012-0112973 | 10/2012 |
| WO | WO 2004/022047 | 3/2004 |
| WO | WO 2006/076681 | 7/2006 |
| WO | WO 2008/013764 | 1/2008 |
| WO | WO 2008/157537 | 12/2008 |
| WO | WO 2009/108999 | 9/2009 |
| WO | WO 2013/071077 | 5/2013 |

OTHER PUBLICATIONS

Debard et al., Diabetologia, 2004, 47, p. 917-925. (Year: 2004).*
Taylor et al., Nature Reviews Genetics, 2005, 6, p. 389-402. (Year: 2005).*
Amaral et al., Journal of Inborn Errors of Metabolism & Screening, 2017, 5, p. 1-7. (Year: 2017).*
Aires et al., *Stilbenes and resveratrol metabolites improve mitochondrial fatty acid oxidation defects in human fibroblasts*, 9(79) Orphanet Journal of Rare Diseases 1-13 (2014).
Andreux et al., *Pharmacological approaches to restore mitochondrial function*, 12 Nature Reviews 465-483 (Jun. 2013).
Bastin et al., *Activation of Peroxisome Proliferator-Activated Receptor Pathway Stimulates the Mitochondrial Respiratory Chain and Can Correct Deficiencies in Patients' Cells Lacking Its Components*, 93(4) J. Clin. Endocrinol. Metab. 1433-1441 (Apr. 2008).
Bastin et al., *Exposure to resveratrol triggers pharmacological correction of fatty acid utilization in human fatty acid oxidation-deficient fibroblasts*, 20(10) Human Molecular Genetics 2048-2057 (2011).
Bhatt et al., *Resveratrol supplementation improves glycemic control in type 2 diabetes mellitus*, 32 Nutrition Research 537-541 (2012).
Bonnefont et al., *Bezafibrate for an Inborn Mitochondrial Beta-Oxidation Defect*, 360(8) N. Engl. J. Med. 838-840 (Feb. 19, 2009).
Bonnefont et al., *Long-Term Follow-Up of Bezafibrate Treatment in Patients With the Myopathic Form of Carnitine Palmitoyltransferase 2 Deficiency*, 88(1) Clinical Pharmacology & Therapeutics 101-108 (Jul. 2010).
Chaturvedi et al., *Mitochondrial Diseases of the Brain*, 63 Free Radical Biology and Medicine 1-29 (2013).
Chaturvedi et al., *Mitochondria targeted therapeutic approaches in Parkinson's and Huntington's diseases*, 55 Molecular and Cellular Neuroscience 101-114 (2013).
Djouadi et al., *Bezafibrate increases very-long-chain acyl-CoA dehydrogenase protein and mRNA expression in deficient fibroblasts and is a potential therapy for fatty acid oxidation disorders*, 14(18) Human Molecular Genetics 2695-2703 (2005).
Djouadi et al., *Correction of Fatty Acid Oxidation in Carnitine Palmitoyl Transferase 2-Deficient Cultured Skin Fibroblasts by Bezafibrate*, 54(4) Pediatric Research 446-451 (2003).
Djouadi et al., *Peroxisome Proliferator Activated Receptor δ (PPARδ) Agonist But Not PPARα Corrects Carnitine Palmitoyl Transferase 2 Deficiency in Human Muscle Cells*, 90(3) The Journal of Clinical Endocrinology & Metabolism 1791-1797 (2005).
Eaton et al., *Mammalian mitochondrial β-oxidation*, 320 Biochem J. 345-357 (1996).

(Continued)

*Primary Examiner* — Jonathan S Lau
(74) *Attorney, Agent, or Firm* — Buchanan Ingersoll & Rooney PC (57) ABSTRACT

The present invention relates to the combined use of bezafibrate and of resveratrol or resveratrol derivatives for the treatment of diseases involving a mitochondrial energy dysfunction, and also to a pharmaceutical kit comprising both bezafibrate and resveratrol or resveratrol derivatives. The combination is more particularly used in the treatment of moderate defects of β-oxidation of long-chain fatty acids or of the respiratory chain of mitochondria.

6 Claims, 3 Drawing Sheets

(56) References Cited

OTHER PUBLICATIONS

Johri et al., *Pharmacologic activation of mitochondrial biogenesis exerts widespread beneficial effects in a transgenic mouse model of Huntington's disease*, 21(5) Human Molecular Genetics 1124-1137 (2012).
Kompare et al., *Mitochondrial Fatty-Acid Oxidation Disorders*, 15 Seminars in Pediatric Neurology 140-149 (2008).
Lagouge et al., *Resveratrol Improves Mitochondrial Function and Protects against Metabolic Disease by Activating SIRT1 and PGC-1α*, 127 Cell 1109-1122 (Dec. 15, 2006).
Papa et al., *Complex I deficiencies in neurological disorders*, 19(1) Trends in Molecular Medicine 61-69 (Jan. 2013).
Patti et al., *The Role of Mitochondria in the Pathogenesis of Type 2 Diabetes*, 31(3) Endocrine Reviews 364-395 (Jun. 2010).
Rötig et al., *Genetic Features of Mitochondrial Respiratory Chain Disorders*, 14 J. Am. Soc. Nephrol. 2995-3007 (2003).
Timmers et al., *Calorie Restriction-like Effects of 30 Days of Resveratrol Supplementation on Energy Metabolism and Metabolic Profile in Obese Humans*, 14 Cell Metabolism 612-622 (Nov. 2, 2011).
Vafai et al., *Mitochondrial disorders as windows into an ancient organelle*, 491 Nature 374-382 (Nov. 15, 2012).
International Search Report dated Apr. 9, 2015, in corresponding PCT Application No. PCT/EP2014/078910.
G. Krey et al., *Fatty Acids, Eicosanoids, and Hypolipidemic Agents Identified as Ligands of Peroxisome Proliferator-Activated Receptors by Coactivator-Dependent Receptor Ligand Assay*, 11 Molecular Endocrinology 779-791 (1997).

\* cited by examiner

Palmitate oxidation in control fibroblasts and in fibroblasts of a patient deficient in LCHAD

Figure 3

Oxygen uptake of control fibroblasts and of fibroblasts deficient in respiratory chain complex IV (mutated COX10 gene)

Figure 4

COMBINATION OF BEZAFIBRATE AND OF RESVERATROL OR RESVERATROL DERIVATIVES FOR THE TREATMENT AND PREVENTION OF DISEASES INVOLVING A MITOCHONDRIAL ENERGY DYSFUNCTION

CROSS-REFERENCE TO RELATED APPLICATIONS

This application is a U.S. National Stage Application pursuant to 35 U.S.C. § 371 of International Patent Application PCT/EP2014/078910, filed on Dec. 19, 2014, and published as WO 2015/092043 on Jun. 25, 2015, which claims priority to French Patent Application 1363027, filed on Dec. 19, 2013, all of which are incorporated herein by reference in their entireties for all purposes.

FIELD OF THE INVENTION

The present invention is in the field of so-called "mitochondrial" diseases" involving mitochondrial energy dysfunction. It relates to the combined use of bezafibrate and of resveratrol or certain derivatives thereof for treating these diseases, and also to a pharmaceutical kit comprising both bezafibrate and resveratrol or certain resveratrol derivatives. The combination is more particularly used for treating moderate mitochondrial long-chain fatty acid β-oxidation or respiratory chain deficiencies.

PRIOR ART

The main function of mitochondria is the production of metabolic energy, in the form of ATP, required by cells for many functions, and in particular, in muscles, for muscle contraction. This process involves, among other things: i) mitochondrial long-chain fatty acid β-oxidation (hereinafter referred to as "β-oxidation"), which produces acetyl coenzyme A from fatty acids, and ii) oxidative phosphorylation (OXPHOS), which produces ATP within the mitochondrial respiratory chain, from reduced equivalents (NADH, $FADH_2$) resulting from β-oxidation, and from oxidation of acetyl-coenzyme A.

Many enzymes and proteins are involved in these processes. β-Oxidation enzymes and proteins, and the very large majority of respiratory chain proteins and enzymes, are encoded by the nuclear genome. Moreover, a small number of respiratory chain proteins are encoded by mitochondrial DNA.

Mutations of the genes encoding these various enzymes and proteins can cause mitochondrial energy dysfunction at the origin of a wide range of clinical manifestations.

Certain mutations lead to a "severe" deficiency of mitochondrial metabolic energy production, thus putting the mutated subject's prognosis of survival in danger. Other mutations lead to a "moderate" deficiency, not putting the mutated subject's prognosis of survival in danger, but causing relatively disabling symptoms. In the case of moderate β-oxidation deficiencies, the diseases are well characterized in clinical and biological terms and cause the appearance of myopathy with muscle stiffness, exertion intolerance, and episodes of muscle destruction (or rhabdomyolysis) starting in adolescence, or in young adults. The potential complications (renal failure requiring hospitalization) and the fact that these muscle attacks can occur in response to even moderate physical exercise, leads most patients to permanently self-limit their physical activity in all areas of everyday life, leading to substantial deterioration of their quality of life. In the case of moderate respiratory chain deficiencies, the phenotypes are less stereotyped, and more variable. However, these moderate respiratory chain deficiencies can also include myopathy with muscle stiffness, myalgia, exertion intolerance, and episodes of muscle destruction (or rhabdomyolysis), as well as other symptoms able to affect many other organs (in particular the heart, the nervous system, and the digestive system).

In the very large majority of cases, these diseases remain without treatment at the present time. Indeed, for β-oxidation deficiencies, the care offered is exclusively nutritional (high-glucose, low-fat diet) and behavioral (limits on fasting and exercise), and has little or no efficacy. For respiratory chain deficiencies, care is essentially "supportive," with the administration of vitamins, cofactors, antioxidants, etc., possibly associated with behavioral measurements, but there is no scientific or clinical proof of the efficacy of these interventions in the very large majority of cases. There is thus a genuine need and a high patient demand for treating these deficiencies, amplified by recent evidence of a significant incidence of respiratory chain deficiencies (1/5000 to 1/8000 births).

In addition to these rare diseases of genetic origin, mitochondrial energy dysfunctions have been observed in many other pathologies, and in particular in metabolic diseases (in particular type II diabetes and obesity, see Andreux et al. Nat Rev Drug Discov. 2013 June; 12(6):465-83) and in certain neurodegenerative diseases (in particular in Parkinson's disease, Alzheimer's disease, Huntington's disease, amyotrophic lateral sclerosis, Friedreich's ataxia and Charcot-Marie-Tooth disease (see Andreux et al. Nat Rev Drug Discov. 2013 June; 12(6):465-83; Chaturvedi et al. Mol Cell Neurosci. 2013 Jul. 55:101-14; and Chaturvedi et al. Free Radic Biol Med. 2013 October; 63:1-29)).

Here again, these are pathologies not benefiting at present from satisfactory treatments.

One strategy envisaged for treating and preventing these pathologies is to increase the activity of mitochondrial enzymes involved in energy production by stimulating their production.

Thus, in the context of moderate mitochondrial β-oxidation or respiratory chain deficiencies of genetic origin, the inventors previously showed that bezafibrate (BZ) and resveratrol (RSV) could each individually induce an increase in the quantity of mutated protein and improve or even correct certain moderate β-oxidation or respiratory chain deficiencies (see Djouadi et al. Pediatr Res, 2003, 54:446-51; Djouadi et al. J. Clin Endocrinol. Metab, 2005, 90:1791-1797; Djouadi et al. Hum Mol Genet, 2005, 14:2695-2703; Bastin et al. J Clin Endocrinol Metab, 2008, 93:1433-1441; Bonnefont et al. N Engl J Med, 2009 360; 8; Bonnefont et al. Clin Pharmacol Ther, 2010, 88:101-108; and Bastin et al. Hum. Mol Genet. 2011, 20:2048-2057). Certain RSV derivatives have also been shown as having the same properties of RSV in moderate β-oxidation deficiencies (Aires V, et al. Orphanet J Rare Dis. 2014 Jun. 5; 9:79).

Similarly, BZ and RSV have each been shown as having beneficial effects in vivo in animal models and/or in humans concerning the following diseases: type II diabetes (see Andreux et al. Nat Rev Drug Discov. 2013 June; 12(6):465-83; Bhatt et al. Nutr. Res. 32, 537-541 (2012)), obesity (Andreux et al. Nat Rev Drug Discov. 2013 June; 12(6): 465-83; Timmers et al. Cell Metab. 2011 Nov. 2; 14(5):612-22), Huntington's disease (see Johri et al. 2012. Hum. Mol. Genet. 21, 1124-1137; Chaturvedi et al. Mol Cell Neurosci. 2013 Jul. 55:101-14; and Chaturvedi et al. Free Radic Biol Med. 2013 October; 63:1-29), and Parkinson's disease (see Chaturvedi et al. Mol Cell Neurosci. 2013 Jul. 55:101-14; and Chaturvedi et al. Free Radic Biol Med. 2013 October; 63:1-29).

There is nevertheless a need for new therapies for diseases involving mitochondrial energy dysfunction. In particular, in the experiments described above, the BZ and the RSV were generally used at high doses. Although these molecules are not associated with strong side effects, the administration of high doses of medicinal products is never desirable. Moreover, decreasing the doses administered also reduces the cost of the treatment.

In the prior art, BZ and RSV are described as two molecules the pharmacological effects of which lead ultimately to the activation of a common target, namely the transcription coactivator PGC1 alpha ("peroxisome proliferator-activated receptor γ coactivator 1 alpha," see Johri et al. 2012. Hum. Mol. Genet. 21, 1124-1137; Bastin et al. J Clin Endocrinol Metab, 2008, 93:1433-1441; Lagouge et al. Cell 127, 1109-1122; Bastin et al. Hum. Mol Genet. 2011, 20:2048-2057). Thus, according to the prior art, treatment with bezafibrate alone, or resveratrol alone, would increase PGC-1α activity, and it is this mechanism which would trigger increased expression of genes encoding mitochondrial respiratory chain or β-oxidation enzymes. According to this hypothesis, the skilled person could not anticipate any functional interaction between the two molecules and could expect that the two molecules have similar effects, and that the administration in combination of the two molecules leads at best to additive effects, or even leads to no amplification of the effect of each of the molecules used alone. Furthermore, if each of the molecules has been tested alone in many diseases involving mitochondrial energy dysfunction, no research team has up to now suggested combining these two molecules in the context of the treatment or the prevention of any of these diseases.

SUMMARY OF THE INVENTION

Surprisingly, in the context of the present invention, the inventors found that the combined use of BZ and RSV generates synergistic effects, thus making it possible to obtain a functional response of increased mitochondrial energy production functions at doses of BZ and RSV much lower than those effective for each of the molecules used alone. More particularly, the inventors showed that the pharmacological effects of BZ on cells of patients having moderate deficiency in CPT2, VLCAD, or LCHAD (β-oxidation enzymes) or in COX10 (respiratory chain complex IV) are potentiated by the addition of RSV, thus leading to synergy of the two compounds and to better correction of deficiencies of β-oxidation or respiratory chain enzymes by the combination (BZ+RSV), compared with the effects of BZ or RSV alone.

In a first aspect, the present invention thus relates to a combination of bezafibrate and of resveratrol, for use as a medicinal product.

The invention further relates to a combination of bezafibrate and of resveratrol, for use in the treatment or prevention of diseases involving mitochondrial energy dysfunction.

In a preferred embodiment, the disease involving mitochondrial energy dysfunction is characterized by moderate deficiency in mitochondrial long-chain fatty acid β-oxidation, or by moderate deficiency of the mitochondrial respiratory chain. These moderate deficiencies are advantageously associated with the presence of at least one mutation on each allele of a gene encoding an enzyme of the mitochondrial long-chain fatty acid β-oxidation process (in particular CPT2, VLCAD and LCHAD) or of a gene encoding an enzyme or a protein (in particular a subunit or an assembly factor of complexes I to IV) essential to mitochondrial respiratory chain function. These mutations can be carried by mitochondrial DNA or nuclear DNA.

In another preferred embodiment, the disease involving mitochondrial energy dysfunction is selected from metabolic diseases (in particular type II diabetes and obesity) and neurodegenerative diseases (in particular Parkinson's disease, Alzheimer's disease, Huntington's disease, amyotrophic lateral sclerosis, Friedreich's ataxia and Charcot-Marie-Tooth disease).

In a second aspect, the invention also relates to a pharmaceutical kit comprising bezafibrate and resveratrol. Bezafibrate and resveratrol can be present in the kit in a single formulation or in two distinct formulations.

DETAILED DESCRIPTION OF THE INVENTION

Definitions

By "bezafibrate" or "BZ" is meant 2-(4-(2-((4-chlorobenzoyl)amino)ethyl)phenoxy)-2-methylpropanoic acid (CAS no. 41859-67-0) of formula (I) below:

(I)

By "resveratrol," "trans-resveratrol," "RSV" or "trans-RSV" is meant 5-[(E)-2-(4-hydroxyphenyl)-ethenyl]benzene-1,3-diol (CAS no. 501-36-0) of formula (II) below:

By "cis-resveratrol" or "cis-RSV" is meant 5-[(Z)-2-(4-hydroxyphenyl)-ethenyl]benzene-1,3-diol (CAS no. 61434-67-1) of formula (III) below:

By "dihydro-resveratrol," "dihydro-RSV", "dihydro-trans-resveratrol" or "dihydro-trans-RSV" is meant 5-[2-(4-hydroxyphenyl)ethyl]benzene-1,3-diol of formula (III) below:

By "piceid", "trans-piceid", "resveratrol-3-O-glucoside" or "trans-resveratrol-3-O-glucoside" is meant 2-[3-hydroxy-5-[(E)-2-(4-hydroxyphenyl)ethenyl]phenoxy]-6-(hydroxymethyl)oxane-3,4,5-triol (CAS no. 27208-80-6) of formula (V) below:

cis-Resveratrol, dihydro-resveratrol and piceid are all derivatives similar to resveratrol and share high structural homology. These derivatives have also been shown as having the same properties of inducing an increase in the amount of mutated protein and of improving or even correcting certain moderate β-oxidation deficiencies (Aires V, et al. Orphanet J Rare Dis. 2014 Jun. 5; 9:79).

By "simultaneous administration" is meant both the administration in the form of a single pharmaceutical formulation associating the two active ingredients BZ and RSV, and the separate administration of two distinct pharmaceutical formulations each containing one of the two active ingredients simultaneously or separated by a very short interval (at most about 1 hour).

By "disease involving mitochondrial energy dysfunction" is meant any disease in which is observed a moderate deficiency in at least one mitochondrial ATP production process, and in particular in long-chain fatty acid β-oxidation (also called "β-oxidation" in the present description) which produces acetyl coenzyme A from fatty acids or in the mitochondrial respiratory chain, in at least certain cell types (in particular fibroblasts, myoblasts, myotubes), or in at least certain tissues, such as for example skeletal muscle, white adipose tissue, liver, pancreas (Patti et al. Endocrine Reviews, 2010, 31:364-395), or brain (Andreux et al. Nat Rev Drug Discov. 2013 June; 12(6):465-83)

By "moderate deficiency" is meant that the process involved in mitochondrial ATP production that is deficient nevertheless has in the subject's cells (in particular fibroblasts) a residual activity of at least 30%, preferably at least 35%, preferably at least 40%, preferably at least 45%, preferably at least 50%, of the activity of the same process in healthy control cells.

The residual activity of a test subject's cells in a mitochondrial ATP production process can be measured with various in vitro tests comparing the activity of the test subject's cells with that of cells of a healthy control subject. The percent residual activity (or "residual activity") can then be calculated by the following formula:

$$\text{Residual activity} = \frac{\text{activity in test cells}}{\text{activity in healthy control cells}} \times 100$$

In particular, concerning β-oxidation, the residual activity of a test subject's cells can be measured in vitro by measuring palmitate β-oxidation in the test subject's cells and in the cells of a healthy control subject, and by calculating percent residual activity according to the following formula:

$$\text{Residual } \beta\text{-oxidation activity} = \frac{\text{palmitate } \beta\text{-oxidation rate in test cells}}{\text{palmitate } \beta\text{-oxidation rate in healthy control cells}} \times 100$$

Cellular palmitate β-oxidation activity can be measured with any suitable technology known to persons skilled in the art. That can in particular be achieved by using tritiated palmitate complexed with BSA (bovine albumin serum), which is added to the cells to be tested. After incubation, the addition of trichloroacetic acid (TCA) in a supernatant sample makes it possible to precipitate unmetabolized complexes (BSA/tritiated palmitate), which are excluded by centrifugation. The measurement of tritium present in the supernatant after centrifugation and exclusion of unmetabolized complexes (BSA/tritiated palmitate) makes it possible to determine the amount of palmitate metabolized by the cells. A precise example of a protocol for implementing this process for measuring palmitate β-oxidation activity is described in Example 1.

In a preferred embodiment, the combination of BZ and RSV is administered to a subject whose cells have palmitate β-oxidation activity of at least 30%, preferably at least 35%, preferably at least 40%, preferably at least 45%, preferably at least 50%, of the activity of this same process in healthy control cells. Advantageously, the combination of BZ and RSV is administered to a subject whose cells have palmitate β-oxidation activity in a test using tritiated palmitate complexed with BSA of at least 30%, preferably at least 35%, preferably at least 40%, preferably at least 45%, preferably at least 50%, of the activity of this same process in the same test in healthy control cells. This is referred to as "moderate deficiency in mitochondrial long-chain fatty acid β-oxidation." These moderate deficiencies in mitochondrial long-chain fatty acid β-oxidation are pathologies well-known to persons skilled in the art (Eaton S, et al. Biochem J. 1996 Dec. 1; 320 (Pt 2):345-57; Kompare M, et al. Semin Pediatr Neurol. 2008 September; 15(3):140-9).

Concerning the respiratory chain, the residual activity of a subject's cells can be measured in vitro by measuring the oxygen uptake in the test subject's cells and in the cells of a healthy control subject, and by calculating the percent residual activity according to the following formula:

$$\text{Respiratory chain residual activity} = \frac{\text{oxygen uptake rate in test cells}}{\text{oxygen uptake rate in healthy control cells}} \times 100$$

The measurement of oxygen uptake can be carried out by any suitable technique known to persons skilled in the art. A polarography technique can in particular be used. It can also and advantageously be carried out using technology based on the detection of fluorescence in culture medium containing the test subject's cells and in culture medium containing the cells of a healthy control subject of two fluorescent probes added to the culture medium, one called the "indicator" and whose fluorescence intensity depends on the oxygen content of the medium in which it is located, and the other called the "reference" and whose fluorescence intensity is insensitive to the oxygen content of the medium in which it is located. The ratio of fluorescence intensities between these two probes makes it possible to calculate the cells' oxygen uptake. This ratio can be normalized by the use of reference measurements in cell-free media with a stable and low ("0% $O_2$" condition) or high ("100% $O_2$" condition) oxygen content, respectively.

This technology uses in particular culture plates covered with polymer into which the two fluorescent probes, "indicator" and "reference," are integrated. The sample to be tested (cells to be tested taken up in culture medium), a control sample (healthy cells taken up in the same culture medium), and control samples with a stable and low ("0% $O_2$" condition) or high ("100% $O_2$" condition) oxygen content, respectively, are distributed on the culture plate, covered with a product preventing any exchange of air between the sample and the ambient air (mineral oil in particular), and the fluorescence kinetics of the two probes (indicator and reference) are measured in the various wells. The fluorescence values thus measured make it possible to calculate oxygen pressure (p$O_2$), according to the following formula:

$$pO_2 = 100\left(\frac{k_0}{I_R} - 1\right) \Big/ \left(\frac{k_0}{k_{100}} - 1\right)$$

where $k_0$ v is the fluorescence ratio between the indicator probe and the reference probe under the 0% $O_2$ condition, $k_{100}$ is the fluorescence ratio between the indicator probe and the reference probe under the 100% $O_2$ condition, and $I_R$ is the fluorescence ratio between the indicator probe and the reference probe under the condition tested (patient's cell sample or control sample).

The oxygen uptake rate (or "OUR") thus corresponds to the absolute value of the slope of the line representing p$O_2$ as a function of time. A precise example of a protocol for implementing this oxygen uptake measurement technology is described in Example 2.

In a preferred embodiment, the combination of BZ and RSV is administered to a subject whose cells have oxygen uptake activity of at least 30%, preferably at least 35%, preferably at least 40%, preferably at least 45%, preferably at least 50%, of the activity of this same process in healthy control cells. Advantageously, the combination of BZ and RSV is administered to a subject whose cells have oxygen uptake activity in a test using the combination of two fluorescent probes added to the culture medium, one called the "indicator" and whose fluorescence intensity depends on the oxygen content of the medium in which it is located, and the other called the "reference" and whose fluorescence intensity is insensitive to the oxygen content of the medium in which it is located, of at least 30%, preferably at least 35%, preferably at least 40%, preferably at least 45%, preferably at least 50%, of the activity in the same test of this same process in healthy control cells. This is referred to as "moderate mitochondrial respiratory chain deficiency." These moderate mitochondrial respiratory chain deficiencies are pathologies well-known to persons skilled in the art (Rötig A, Munnich A. Genetic features of mitochondrial respiratory chain disorders. J Am Soc Nephrol. 2003 December; 14(12):2995-3007).

An agent that uncouples the mitochondrial respiratory chain (and thus mitochondrial oxygen uptake) from ATP production (called an "uncoupling agent," such as dinitrophenol, carbonyl cyanide m-chlorophenylhydrazone (CCCP), and carbonyl cyanide p-trifluoromethoxyphenylhydrazone (FCCP)) can be added to the samples of test cells and control cells in order to increase oxygen uptake and thus to more easily demonstrate a deficiency.

In a particular embodiment, the combination of BZ and RSV is furthermore administered to a subject whose cells have significantly deficient activity in a process involved in mitochondrial ATP production, i.e., to a subject whose cells have residual activity of at most 85%, preferably of at most 80%, indeed of at most 75% of the activity of this same process in healthy control cells. If the process involved in mitochondrial ATP production that is deficient is the mitochondrial long-chain fatty acid β-oxidation process, the combination of BZ and RSV is preferably administered to a subject whose cells have residual palmitate β-oxidation activity of at most 85%, preferably of at most 80%, indeed of at most 75% of palmitate β-oxidation activity in healthy control cells. Advantageously, palmitate β-oxidation activity is measured with the test using the tritiated palmitate complexed with BSA described above. If the process involved in mitochondrial ATP production that is deficient is the mitochondrial respiratory chain, the combination of BZ and RSV is preferably administered to a subject whose cells have oxygen uptake of at most 85%, preferably of at most 80%, indeed of at most 75% of the oxygen uptake in healthy control cells. Advantageously, oxygen uptake is measured with the test using the combination of two fluorescent probes added to the culture medium, one called the "indicator" and whose fluorescence intensity depends on the oxygen content of the medium in which it is located, and the other called the "reference" and whose fluorescence intensity is insensitive to the oxygen content of the medium in which it is located, as described above.

This embodiment is particularly adapted to mitochondrial energy dysfunctions not being associated with the presence of mutations in a gene encoding an enzyme of the mitochondrial long-chain fatty acid β-oxidation process (in particular CPT2, VLCAD and LCHAD) or in a gene encoding an enzyme or a protein of the mitochondrial respiratory chain (in particular a subunit or an assembly factor of complexes I to IV). Preferably, the combination of BZ and RSV is administered to a subject suffering from a disease involving mitochondrial energy dysfunction selected from metabolic diseases or neurodegenerative diseases, and whose cells have residual activity in a process involved in mitochondrial ATP production of at most 85%, preferably of at most 80%, indeed of at most 75% of the activity of this same process in healthy control cells. As described above, the subject to whom the combination of BZ and RSV is administered preferably suffers from moderate deficiency in a deficient process involved in mitochondrial ATP production, i.e., the residual activity of the deficient process involved in mitochondrial ATP production is preferably at least 30%, preferably at least 35%, preferably at least 40%, preferably at least 45%, preferably at least 50%, of the activity of this same process in healthy control cells.

By "treatment" is meant a clinical or biochemical improvement observed in the patient's pathology.

In the context of moderate mitochondrial β-oxidation deficiencies, the main clinical symptoms are myopathy, with muscle stiffness, myalgia, exertion intolerance, and episodes of muscle destruction (or rhabdomyolysis). In biochemical terms, these deficiencies are characterized by reduced activity (as defined above) of β-oxidation of the patients' cells (and in particular fibroblasts) compared to cells of healthy subjects. Consequently, in the context of moderate mitochondrial β-oxidation deficiencies, the term "treatment" refers to an improvement in β-oxidation function of the patient's cells and/or to a reduction in the frequency and/or intensity of muscle stiffness and/or of episodes of myalgia and/or of rhabdomyolysis.

In the context of moderate mitochondrial respiratory chain deficiencies, the main clinical symptoms can also be myopathy with muscle stiffness, myalgia, exertion intolerance, and episodes of muscle destruction (or rhabdomyolysis). However, other symptoms can also be observed affecting a wide range of organs (in particular the heart, the nervous system, and the digestive system). In biochemical terms, these deficiencies are characterized by reduced respiration activity (as defined above) of the patients' cells (and in particular fibroblasts) compared to cells of healthy subjects. Consequently, in the context of moderate mitochondrial respiratory chain deficiencies, the term "treatment" refers to improvement of the cellular respiration function of the patient's cells and/or to a reduction in the frequency and/or intensity of muscle stiffness, of episodes of myalgia and/or of rhabdomyolysis, or of cardiac, neurological or digestive attacks.

By "prevention" is meant the fact of preventing or delaying the occurrence or decreasing the intensity of the clinical or biochemical manifestations associated with the disease.

In the context of moderate mitochondrial β-oxidation deficiencies, the term "prevention" thus refers to the fact of preventing or delaying the occurrence or decreasing the intensity of the loss of β-oxidation activity of the patient's cells, and/or of preventing or delaying the occurrence or decreasing the intensity of muscle stiffness and/or of episodes of myalgia and/or of rhabdomyolysis.

In the context of moderate mitochondrial respiratory chain deficiencies, the term "prevention" thus refers to the fact of preventing or delaying the occurrence or decreasing the intensity of the loss of respiration activity of the patient's cells and/or of preventing or delaying the occurrence or decreasing the intensity of muscle stiffness, of episodes of myalgia and/or of rhabdomyolysis, or of cardiac or neurological or digestive attacks.

By "effective amounts" of BZ and of RSV or a derivative thereof (cis-RSV, dihydro-RSV, or piceid) is meant respective amounts allowing, in combination, the treatment or prevention of a disease involving mitochondrial energy dysfunction in a patient.

Combination of bezafibrate (BZ) and of resveratrol (RSV) or a derivative thereof, for simultaneous or sequential use as a medicinal product Despite the teachings of the prior art, according to which both BZ and RSV target PGC-1α, the inventors surprisingly found that the combined use of BZ and RSV generates synergistic effects, thus making it possible to obtain a functional response of increased mitochondrial energy production functions at doses of BZ and RSV much lower than those effective for each molecule used alone. In particular, this synergy was shown in cells of patients having moderate deficiency in CPT2, VLCAD, LCHAD (β-oxidation enzymes), or in COX10 (respiratory chain complex IV). The discovery by the inventors that, unlike other fibrates, bezafibrate is capable of correcting CPT2 deficiency makes the specific combination bezafibrate/resveratrol particularly effective for treating or preventing diseases involving mitochondrial energy dysfunction.

In a first aspect, the present invention thus relates to a combination 1) of bezafibrate and 2) of resveratrol, cis-resveratrol, dihydro-resveratrol, piceid or mixtures thereof (advantageously resveratrol), for use as a medicinal product.

In particular, the present invention relates to a combination 1) of bezafibrate and 2) of resveratrol, cis-resveratrol, dihydro-resveratrol, piceid or mixtures thereof (advantageously resveratrol), for use in the treatment or prevention of diseases involving mitochondrial energy dysfunction.

The present invention also relates to the use in combination 1) of BZ and 2) of RSV, cis-RSV, dihydro-RSV, piceid or mixtures thereof (advantageously RSV), for preparing a medicinal product intended for the treatment or prevention of diseases involving mitochondrial energy dysfunction.

The present invention also relates to the use in combination 1) of BZ and 2) of RSV, cis-RSV, dihydro-RSV, piceid or mixtures thereof (advantageously RSV), for treating or preventing diseases involving mitochondrial energy dysfunction.

The present invention also relates to a method of therapeutic treatment of a disease involving mitochondrial energy dysfunction in a patient in need thereof, comprising administering to said patient effective amounts in combination 1) of BZ and 2) of RSV, cis-RSV, dihydro-RSV, piceid or mixtures thereof (advantageously RSV).

Diseases Involving Mitochondrial Energy Dysfunction

Diseases involving mitochondrial energy dysfunction are defined above and include:
rare genetic diseases, associated with the presence of at least one mutation, preferably of at least two mutations, in a gene encoding an enzyme or a protein involved in one mitochondrial ATP production process, and in particular in the β-oxidation process or in the respiratory chain, and mainly acquired diseases, although possibly having a genetic component, which are much more frequent and generally associated with metabolic problems (metabolic diseases) and/or with aging (neurodegenerative diseases).

In a preferred embodiment of the invention, the disease involving mitochondrial energy dysfunction is characterized by moderate deficiency in mitochondrial long-chain fatty acid β-oxidation. As indicated above, these moderate deficiencies in mitochondrial long-chain fatty acid β-oxidation are pathologies well-known to persons skilled in the art (Eaton S, et al. Biochem J. 1996 Dec. 1; 320 (Pt 2):345-57; Kompare M, et al. Semin Pediatr Neurol. 2008 September; 15(3):140-9). Advantageously, the moderate deficiency in mitochondrial long-chain fatty acid β-oxidation is associated with the presence of at least one mutation on each allele of a gene encoding an enzyme of the mitochondrial long-chain fatty acid β-oxidation process.

Indeed, all of the described β-oxidation deficiencies involve autosomal recessive transmission, i.e., subjects suffering from β-oxidation deficiencies are carrying two mutated alleles (one of maternal origin, the other of paternal origin) of a gene encoding an enzyme of the mitochondrial long-chain fatty acid β-oxidation process. The mutation can be identical on both mutated alleles, in which case the subject has a homozygous genotype. Alternatively, the mutation can be distinct on both mutated alleles, the subject then having a heterozygous genotype. The expression "on each allele" thus refers to the presence of a mutation on both the allele of maternal origin and the allele of paternal origin, in homozygous form (identical mutation on both mutated alleles) or in heterozygous form (distinct mutation on both mutated alleles).

The β-oxidation process involves many enzymes, which are likely to lead to β-oxidation deficiency in the event of mutation(s) (see Eaton et al. Biochem J. 1996 Dec. 1; 320 (Pt 2):345-57). The enzymes involved in β-oxidation for which mutations leading to moderate β-oxidation deficiency are most frequent are the following: carnitine palmitoyltransferase type 2 (hereinafter referred to as "CPT2"), very long-chain acyl-CoA dehydrogenase (hereinafter referred to as "VLCAD"), and long-chain 3-hydroxyacyl CoA dehydrogenase (hereinafter referred to as "LCHAD"). Consequently, in a preferred embodiment of the present invention, the treated subject suffers from moderate deficiency in mitochondrial long-chain fatty acid β-oxidation associated with at least one mutation on each allele, in the homozygous state (identical mutation on both mutated alleles) or the heterozygous state (distinct mutation on both mutated alleles), of one of the genes encoding one of the following enzymes: CPT2, VLCAD, and LCHAD. However, moderate β-oxidation deficiencies associated with a mutation on each allele, in the homozygous state or the heterozygous state, of one of the genes encoding another enzyme or protein involved in the β-oxidation process are also the subject of the present invention. Such enzymes or proteins include in particular: carnitine palmitoyltransferase type 1 ("CPT1"), carnitine acylcarnitine translocase, other acyl CoA dehydrogenases (short-chain "SCAD," medium-chain "MCAD," or long-chain acyl-CoA dehydrogenase "LCAD"), mitochondrial trifunctional protein (combining the activities of long-chain 2-enoyl-CoA hydratase, LCHAD, and long-chain 3-oxoacyl-CoA thiolase), short-chain 2-enoyl-CoA hydratase, short-chain 3-oxoacyl-CoA thiolase, electron transfer flavoprotein ("ETF"), electron transfer flavoprotein dehydrogenase (ETFDH, also called ETF-ubiquinone oxidoreductase "ETFQO").

In another preferred embodiment of the invention, the disease involving mitochondrial energy dysfunction is characterized by moderate mitochondrial respiratory chain deficiency. As indicated above, these moderate mitochondrial respiratory chain deficiencies are pathologies well-known to persons skilled in the art (Rötig A, Munnich A. Genetic features of mitochondrial respiratory chain disorders. J Am Soc Nephrol. 2003 December; 14(12):2995-3007). Advantageously, the moderate mitochondrial respiratory chain deficiency is associated with the presence of at least one mutation on each allele of a gene, advantageously nuclear, encoding an enzyme or a protein essential to mitochondrial respiratory chain function.

Genetic deficiencies of the mitochondrial respiratory chain can involve nuclear genes, in which case the known deficiencies also involve, as for β-oxidation deficiencies, autosomal recessive transmission, i.e., subjects suffering from such mitochondrial respiratory chain deficiencies are carrying two mutated alleles (one of maternal origin, the other of paternal origin) of a gene encoding an enzyme or a protein essential to mitochondrial respiratory chain function. The mutation can be identical on both mutated alleles, in which case the subject has a homozygous genotype. Alternatively, the mutation can be distinct on both mutated alleles, the subject then having a heterozygous genotype. As for β-oxidation deficiencies, the expression "on each allele" thus refers to the presence of a mutation on both the allele of maternal origin and the allele of paternal origin, in homozygous form (identical mutation on both mutated alleles) or in heterozygous form (distinct mutation on both mutated alleles).

Genetic deficiencies of the mitochondrial respiratory chain can also involve mitochondrial genes (i.e., genes encoded by mitochondrial DNA) of maternal origin only. In this case, there is only one "allele" in the meaning of the present invention of maternal origin, and the expression "on each allele" thus refers to the presence of a mutation on the allele of maternal origin only. On the other hand, the mitochondrial genome transmitted by the mother can be characterized by a certain degree of heteroplasmy, i.e., all the copies of mitochondrial DNA are not necessarily carrying the mutation. When the deficiency is related to a mitochondrial gene, it is then associated with the presence of at least one mutation in a mitochondrial gene encoding an enzyme or a protein essential to mitochondrial respiratory chain function.

The mitochondrial respiratory chain also involves numerous enzymes and proteins, which are likely to lead to respiratory chain deficiency in the event of mutation(s). This metabolic pathway comprises five enzymatic complexes called complex I ("CI" or "nicotinamide dinucleotide dehydrogenase-ubiquinone oxidoreductase" or "NADH-CoQ reductase," more than 40 subunits), complex II ("CII" or "succinate dehydrogenase-ubiquinone oxidoreductase" or "succinate-CoQ reductase," 4 subunits), complex III ("CIII," or "ubiquinone-cytochrome c oxidoreductase," 11 subunits), complex IV ("CIV" or "cytochrome c oxidase," 13 subunits), and complex V ("CV" or "ATP synthase" or "ATPase," about 16 subunits).

At the present time, in 2013, a certain number of subunits present in each of these complexes, as well as a certain number of other so-called assembly or ancillary proteins essential to the functioning of these complexes, as well as various mutations targeting these proteins and responsible for respiratory chain deficiency, are known to persons skilled in the art (see Vafai et al. 2012, Nature, 491:374-383). However, other proteins essential to respiratory chain function, and other mutations targeting these proteins and leading to respiratory chain deficiency, will in all likelihood be discovered in the coming years.

The most frequently mutated genes leading to respiratory chain deficiency are the structural genes or the assembly genes of complex I (CI), and of complex IV (CIV). Consequently, in a preferred embodiment of the present invention, the treated subject suffers from moderate respiratory chain deficiency associated with the presence of at least one mutation on each allele of one of the genes encoding one of the subunits or one of the proteins essential to the functioning of complexes I to IV, in particular on the genes of complex I: NDUFS1, NDUFS2, NDUFS3, NDUFS4, NDUFS6, NDUFS7, NDUFV1, NDUFV2, ACAD9, and of complex IV: COX10 and SURF1.

However, moderate respiratory chain deficiencies associated with at least one mutation on each allele of other genes encoding one of the subunits or one of the proteins essential to respiratory chain function are also the subject of the present invention and in particular the following genes:

Complex I: NDUFA1, NDUFA2, NDUFA9, NDUFA10, NDUFA11, NDUFA12, NUDFB3, NDUFB9, NDUFS8, NDUFAF1, NDUFAF2, NDUFAF3, NDUFAF4, NDUFAF5, NDUFAF6, FOXRED1, NUBPL, ND1, ND2, ND3, ND4, ND4L, ND5, ND6;

Complex II: SDHA, SDHB, SDHC, SDHD, SDHAF1, SDHAF2;

Complex III: UQCRB, UQCRQ, BCS1L, HCCS, TTC19, CYTB;

Complex IV: COX4I2, COX6B1, COX15, ETHE1, FASTKD2, SCO1, SCO2, COX14, COA5, COX1, COX2;

Complex V: ATP5E, ATPAF2, TMEM70, ATP6, ATP8;

Others: TWINKLE, MTFMT, GFM1, LRPPRC, MPV17, MRPS16, MRPS22, POLG, POLG2, TRMU, TSFM, TUFM, C12orf65, MTPAP, MRPL3, SARS2, YARS2, HARS2, MARS2, AARS2, RARS2, EARS2, DARS2, TACO1, MTO1, RMND1, PNPT1, PUS1, ABCB7, RXN, ISCU, NFU1, BOLA3, GLRX5, DNAJC19, GFER, HSPD1, SPG7, TIMM8A, AIFM1, AFG3L2, DGUOK, RRM2B, SLC25A3, ANT1, SUCLA2, SUCLG1, TK2, TYMP, ADCK3, AGK, COQ2, COQ6, COQ9, DRP1, MFN2, OPA1, PDSS1, PDSS2, TAZ, SERAC1.

In still another embodiment, the disease involving mitochondrial energy dysfunction is selected from metabolic diseases and neurodegenerative diseases.

Indeed, mitochondrial energy dysfunction has been discovered in many metabolic or neurodegenerative diseases. Concerning metabolic diseases, such mitochondrial energy dysfunction has been shown in particular in the context of type II diabetes and obesity (Andreux et al. Nat Rev Drug Discov. 2013 June; 12(6):465-83). Concerning neurodegenerative diseases, mitochondrial energy dysfunction has been shown at least in the following pathologies: Parkinson's disease, Alzheimer's disease, Huntington's disease, amyotrophic lateral sclerosis, Friedreich's ataxia, Charcot-Marie-Tooth disease, and Down syndrome (Andreux et al. Nat Rev Drug Discov. 2013 June; 12(6):465-83; Chaturvedi et al. Mol Cell Neurosci. 2013 Jul. 55:101-14; Chaturvedi et al. Free Radic Biol Med. 2013 October; 63:1-29; and Papa S. et al. Trends Mol Med. 2013 January; 19(1):61-9).

Moreover, BZ or RSV has been suggested as being able to have a beneficial effect on the living conditions and pathology of patients suffering from these diseases (Andreux et al. Nat Rev Drug Discov. 2013 June; 12(6):465-83; Chaturvedi et al. Mol Cell Neurosci. 2013 Jul. 55:101-14; and Chaturvedi et al. Free Radic Biol Med. 2013 October; 63:1-29). It is thus reasonable to believe that the synergistic effects between BZ and RSV observed by the inventors in the context of moderate β-oxidation or respiratory chain deficiencies will also apply in the context of these pathologies, and will thus allow the best care of patients suffering from these diseases.

Thus, in a preferred embodiment of the invention, the metabolic disease is selected from type II diabetes and obesity. In another preferred embodiment of the invention, the neurodegenerative disease is selected from Parkinson's disease, Alzheimer's disease, Huntington's disease, amyotrophic lateral sclerosis, Friedreich's ataxia and Charcot-Marie-Tooth disease, and in particular from Parkinson's disease and Huntington's disease.

Moreover, in a preferred embodiment of the invention, the combination 1) of BZ and 2) of RSV, cis-RSV, dihydro-RSV, piceid or mixtures thereof (advantageously RSV) is intended to be used in the treatment or prevention of metabolic diseases (in particular type II diabetes and obesity) and/or of neurodegenerative diseases (in particular Parkinson's disease, Alzheimer's disease, Huntington's disease, amyotrophic lateral sclerosis, Friedreich's ataxia and Charcot-Marie-Tooth disease, and in particular of Parkinson's disease and Huntington's disease), in subjects suffering from moderate deficiency in mitochondrial long-chain fatty acid β-oxidation or moderate deficiency of the mitochondrial respiratory chain, as described above.

Administration

The administrations of BZ and of RSV, cis-RSV, dihydro-RSV, piceid or mixtures thereof (advantageously RSV) can be simultaneous or sequential, these terms being defined above.

Whether the administration is simultaneous or sequential, the BZ and the RSV, cis-RSV, dihydro-RSV, piceid or mixtures thereof (advantageously RSV) can be administered by any appropriate route of administration, in particular by oral route. In a preferred embodiment, the BZ and the RSV, cis-RSV, dihydro-RSV, piceid or mixtures thereof (advantageously RSV) are both administered by oral route, since it is the recommended route of administration for each of these two active ingredients.

Although there is to date no combined formulation of BZ and of RSV, cis-RSV, dihydro-RSV, piceid or mixtures thereof (advantageously RSV), the development of such a formulation would make it possible to simplify the simultaneous administration of these two active ingredients for patients. The simultaneous administration, as defined above, of one or more BZ tablets and one or more RSV capsules, however, also constitutes a preferred embodiment, since today BZ is available in tablet form and RSV in capsule form.

The synergistic effects shown by the inventors make it possible to reduce significantly the doses of BZ and of RSV, cis-RSV, dihydro-RSV, piceid or mixtures thereof (advantageously RSV) administered to patients. In the prior art, the doses of BZ administered to patients suffering from moderate deficiencies in β-oxidation enzyme CPT2 were 600 mg/day (see Bonnefont et al. N Engl J Med, 2009 360; 8; and Bonnefont et al. Clin Pharmacol Ther, 2010, 88:101-108). When administered alone, the doses of RSV, cis-RSV, dihydro-RSV, piceid or mixtures thereof (advantageously RSV) administered to adult subjects in the prior art generally vary from at least 150 mg/day to more than 1 g/day.

In a preferred embodiment, the dose of BZ administered in combination with RSV, cis-RSV, dihydro-RSV, piceid or mixtures thereof (advantageously RSV) to an adult subject is preferably between 100 and 400 mg/day, and in particular between 100 and 350 mg/day, between 100 and 300 mg/day, between 100 and 250 mg/day, between 100 and 200 mg/day, between 100 and 150 mg/day, between 150 and 400 mg/day, between 150 and 350 mg/day, between 150 and 300 mg/day, between 150 and 250 mg/day, between 150 and 200 mg/day, between 200 and 400 mg/day, between 200 and 350 mg/day, between 200 and 300 mg/day, between 200 and 250 mg/day, between 250 and 400 mg/day, between 250 and 350 mg/day, between 250 and 300 mg/day, between 300 and 400 mg/day, between 300 and 350 mg/day, or between 350 and 400 mg/day. The lowest dose BZ tablets currently available are 200 mg, and the dose of BZ administered in combination with RSV, cis-RSV, dihydro-RSV, piceid or mixtures thereof (advantageously RSV) to an adult subject can thus advantageously be 200 or 400 mg/day. Nevertheless, if lower-dose BZ formulations were available, lower doses could be envisaged.

In a preferred embodiment, the dose of RSV, cis-RSV, dihydro-RSV, piceid or mixtures thereof (advantageously RSV) administered in combination with BZ to an adult subject is significantly lower than 1 g/day and preferably is between 150 and 500 mg/day, and in particular between 150 and 450 mg/day, between 150 and 400 mg/day, between 150 and 350 mg/day, between 150 and 300 mg/day, between 150 and 250 mg/day, between 150 and 200 mg/day, between 200 and 500 mg/day, between 200 and 450 mg/day, between 200 and 400 mg/day, between 200 and 350 mg/day, between 200 and 300 mg/day, between 200 and 250 mg/day, between 250 and 500 mg/day, between 250 and 450 mg/day, between 250 and 400 mg/day, between 250 and 350 mg/day, between 250 and 300 mg/day, between 300 and 500 mg/day, between 300 and 450 mg/day, between 300 and 400 mg/day, between 300 and 350 mg/day, between 350 and 500 mg/day, between 350 and 450 mg/day, between 350 and 400 mg/day, between 400 and 500 mg/day, between 400 and 450 mg/day, or between 450 and 500 mg/day. RSV is currently available in the form of capsules containing variable amounts of RSV ranging from a few tens of mg (in particular 20 or 50 mg) to a few hundreds of mg (in particular 200, 250 or 500 mg), thus making it possible to easily adjust the desired dose. cis-RSV, dihydro-RSV, piceid or mixtures thereof can also be in the form of capsules similar to those existing for RSV.

Advantageously, the doses of BZ and of RSV, cis-RSV, dihydro-RSV, piceid or mixtures thereof (advantageously RSV) administered in combination to an adult subject are preferably:

between 100 and 400 mg/day, and in particular between 100 and 350 mg/day, between 100 and 300 mg/day, between 100 and 250 mg/day, between 100 and 200 mg/day, between 100 and 150 mg/day, between 150 and 400 mg/day, between 150 and 350 mg/day, between 150 and 300 mg/day, between 150 and 250 mg/day, between 150 and 200 mg/day, between 200 and 400 mg/day, between 200 and 350 mg/day, between 200 and 300 mg/day, between 200 and 250 mg/day, between 250 and 400 mg/day, between 250 and 350 mg/day, between 250 and 300 mg/day, between 300 and 400 mg/day, between 300 and 350 mg/day, or between 350 and 400 mg/day for BZ, and between 150 and 500 mg/day, and in particular between 150 and 450 mg/day, 150 and 400 mg/day, between 150 and 350 mg/day, between 150 and 300 mg/day, between 150 and 250 mg/day, between 150 and 200 mg/day, between 200 and 500 mg/day, between 200 and 450 mg/day, between 200 and 400 mg/day, between 200 and 350 mg/day, between 200 and 300 mg/day, between 200 and 250 mg/day, between 250 and 500 mg/day, between 250 and 450 mg/day, between 250 and 400 mg/day, between 250 and 350 mg/day, between 250 and 300 mg/day, between 300 and 500 mg/day, between 300 and 450 mg/day, between 300 and 400 mg/day, between 300 and 350 mg/day, between 350 and 500 mg/day, between 350 and 450 mg/day, between 350 and 400 mg/day, between 400 and 500 mg/day, between 400 and 450 mg/day, or between 450 and 500 mg/day for RSV, cis-RSV, dihydro-RSV, piceid or mixtures thereof (advantageously RSV).

The daily doses mentioned above can be administered, in particular when administration is by oral route, in one or more doses distributed throughout the day. Preferably, the number of daily doses does not exceed three. In particular, the daily dose can be administered in 1, 2, 3, or 4 daily doses. When they are administered in an immediate-release formulation, the BZ and the RSV, cis-RSV, dihydro-RSV, piceid or mixtures thereof (advantageously RSV) have a rather short half-life, which favors several daily doses (2, 3 or 4, in particular 2 or 3) in order to maintain a certain circulating concentration. However, if prolonged-release formulations will be used, one or two daily doses can be sufficient.

Predictive Preclinical Testing Before Administration

A beneficial aspect of the present invention is that it is possible to select, with a preliminary in vitro test, patients likely to benefit from treatment combining 1) BZ and 2) RSV, cis-RSV, dihydro-RSV, piceid or mixtures thereof (advantageously RSV).

Indeed, when one of the mitochondrial ATP production processes is shown to be in moderate deficiency (as defined above) in a patient, then the patient's capacity to respond to treatment combining 1) BZ and 2) RSV, cis-RSV, dihydro-RSV, piceid or mixtures thereof (advantageously RSV) can be predicted by testing in vitro the ability of the combination (BZ+(RSV, cis-RSV, dihydro-RSV, piceid or mixtures thereof (advantageously RSV))) to improve, or even to restore, the activity of the deficient process in the patient's cells.

In particular, in the case of patients suffering from moderate mitochondrial β-oxidation or respiratory chain deficiency, it is possible to predict the efficacy in these patients of the treatment combining 1) BZ and 2) RSV, cis-RSV, dihydro-RSV, piceid or mixtures thereof (advantageously RSV) based on the comparison of mitochondrial β-oxidation or respiratory chain activities in the patient's cells in the absence and in the presence of the combination (BZ+(RSV, cis-RSV, dihydro-RSV, piceid or mixtures thereof (advantageously RSV))). In this context, β-oxidation or respiratory chain activities can be measured with the tests described above in order to establish the existence of moderate deficiency. If the presence of the combination 1) of BZ and 2) of RSV, cis-RSV, dihydro-RSV, piceid or mixtures thereof (advantageously RSV) improves β-oxidation or respiratory chain function in the patient's cells in vitro, then the treatment combining 1) BZ and 2) RSV, cis-RSV, dihydro-RSV, piceid or mixtures thereof (advantageously RSV) should prove effective in treating and preventing the patient's symptoms in vivo. In the opposite case (no significant improvement of the deficient function in vitro), it is probable that the treatment combining 1) BZ and 2) RSV, cis-RSV, dihydro-RSV, piceid or mixtures thereof (advantageously RSV) will be ineffective in the patient.

Thus, in an embodiment of the invention, the patient can be selected from those for whom the combined presence 1)

of BZ and 2) of RSV, cis-RSV, dihydro-RSV, piceid or mixtures thereof (advantageously RSV) improves β-oxidation or respiratory chain activity in the patient's cells in vitro. Preferably, this improvement is observed in vitro for doses 1) of BZ and 2) of RSV, cis-RSV, dihydro-RSV, piceid or mixtures thereof (advantageously RSV) of between 25 and 35 µM (for BZ) and of between 20 and 30 µM (for RSV, cis-RSV, dihydro-RSV, piceid or mixtures thereof (advantageously RSV)).

Pharmaceutical Kit Comprising Bezafibrate and Resveratrol or Resveratrol Derivatives, for Simultaneous or Sequential Administration In a second aspect, the present invention also relates to a pharmaceutical kit comprising 1) bezafibrate and 2) resveratrol, cis-resveratrol, dihydro-resveratrol, piceid or mixtures thereof (advantageously resveratrol).

In the pharmaceutical kit according to the invention, the BZ and the RSV, cis-RSV, dihydro-RSV, piceid or mixtures thereof (advantageously RSV) can be present in the form of a single pharmaceutical formulation associating the two active ingredients 1) BZ and 2) RSV, cis-RSV, dihydro-RSV, piceid or mixtures thereof (advantageously RSV), or of two distinct formulations each comprising one of the active ingredients (thus allowing simultaneous or sequential administration).

In all cases, the dose of BZ is selected so as to allow administration of the daily doses defined above in 1, 2 or 3 daily doses. Thus, the dose of BZ comprised in the pharmaceutical kit according to the invention is advantageously between 33 and 400 mg, and in particular between 33 and 350 mg, between 33 and 300 mg, between 33 and 250 mg, between 33 and 200 mg, between 33 and 150 mg, between 50 and 400 mg, between 50 and 350 mg, between 50 and 300 mg, between 50 and 250 mg, between 50 and 200 mg, between 67 and 400 mg, between 67 and 350 mg, between 67 and 300 mg, between 67 and 250 mg, between 67 and 400 mg, between 83 and 350 mg, between 83 and 300 mg, between 100 and 400 mg, between 100 and 350 mg, or between 117 and 400 mg.

Likewise, the dose of RSV, cis-RSV, dihydro-RSV, piceid or mixtures thereof (advantageously RSV) is selected so as to allow administration of the daily doses defined above in 1, 2 or 3 daily doses. Thus, the dose of RSV, cis-RSV, dihydro-RSV, piceid or mixtures thereof (advantageously RSV) comprised in the pharmaceutical kit according to the invention is advantageously between 50 and 500 mg, and in particular between 50 and 450 mg, between 50 and 400 mg, between 50 and 350 mg, between 50 and 300 mg, between 50 and 250 mg, between 50 and 200 mg, between 67 and 500 mg, between 67 and 450 mg, between 67 and 400 mg, between 67 and 350 mg, between 67 and 300 mg, between 67 and 250 mg, between 83 and 500 mg, between 83 and 450 mg, between 83 and 400 mg, between 83 and 350 mg, between 83 and 300 mg, between 100 and 500 mg, between 100 and 450 mg, between 100 and 400 mg, between 100 and 350 mg, between 117 and 500 mg, between 117 and 450 mg, between 117 and 400 mg, between 133 and 500 mg, between 133 and 450 mg, or between 150 and 500 mg.

Advantageously, the doses 1) of BZ and 2) of RSV, cis-RSV, dihydro-RSV, piceid or mixtures thereof (advantageously RSV) present in the pharmaceutical kit according to the invention are preferably:

between 33 and 400 mg, and in particular between 33 and 350 mg, between 33 and 300 mg, between 33 and 250 mg, between 33 and 200 mg, between 33 and 150 mg, between 50 and 400 mg, between 50 and 350 mg, between 50 and 300 mg, between 50 and 250 mg, between 50 and 200 mg, between 67 and 400 mg, between 67 and 350 mg, between 67 and 300 mg, between 67 and 250 mg, between 67 and 400 mg, between 83 and 350 mg, between 83 and 300 mg, between 100 and 400 mg, between 100 and 350 mg, or between 117 and 400 mg for BZ, and between 50 and 500 mg, and in particular between 50 and 450 mg, between 50 and 400 mg, between 50 and 350 mg, between 50 and 300 mg, between 50 and 250 mg, between 50 and 200 mg, between 67 and 500 mg, between 67 and 450 mg, between 67 and 400 mg, between 67 and 350 mg, between 67 and 300 mg, between 67 and 250 mg, between 83 and 500 mg, between 83 and 450 mg, between 83 and 400 mg, between 83 and 350 mg, between 83 and 300 mg, between 100 and 500 mg, between 100 and 450 mg, between 100 and 400 mg, between 100 and 350 mg, between 117 and 500 mg, between 117 and 450 mg, between 117 and 400 mg, between 133 and 500 mg, between 133 and 450 mg, or between 150 and 500 mg for RSV, cis-RSV, dihydro-RSV, piceid or mixtures thereof (advantageously RSV).

The following examples aim at illustrating the present invention.

EXAMPLES

Example 1: Study of the Effects of Low Doses of Resveratrol (RSV) (20 or 30 µM) in Combination with Low Doses of Bezafibrate (BZ) (25 or 35 µM) in Fibroblasts of Patients Suffering from Moderate β-Oxidation Deficiency The effect of low doses of RSV (20 or 30 µM) in combination with low doses of BZ (25 or 35 µM) in fibroblasts affected by moderate β-oxidation deficiency was studied in two patients suffering from moderate VLCAD deficiency and two patients suffering from moderate CPT2 deficiency.

Patients and Methods

Patients

Patients Deficient in VLCAD:

Patient E3536: Myopathic form of the deficiency; genotype A304T/G439D; β-oxidation value measured on fibroblasts in the absence of treatment: 1.69 nmol/h/mg protein (versus 5.24 in the control) or −68%.

Patient CHA Ma: Myopathic form of the deficiency; genotype V283A/V283A; β-oxidation value measured on fibroblasts in the absence of treatment: 2.74 nmol/h/mg protein (versus 5.24 in the control) or −48%.

Patients Deficient in CPT2:

Patient BRA Ma: Myopathic form of the deficiency; genotype S113L/R124Q; β-oxidation value measured on fibroblasts in the absence of treatment: 3.28 nmol/h/mg protein (versus 5.24 in the control) or −37%.

Patient DIA Ke: Myopathic form of the deficiency; genotype S113L/S38AFsX36; β-oxidation value measured on fibroblasts in the absence of treatment: 2.86 nmol/h/mg protein (versus 5.24 in the control) or −45%.

Treatments Applied

The fibroblasts are grown at 37° C. in complete Ham's F10 medium, i.e., supplemented with 12% fetal calf serum, 100 U/ml penicillin, and 0.1 mg/ml streptomycin, at a concentration of 70,000 cells per ml and per well in 24-well culture dishes. Twenty-four hours after seeding, stock solutions of RSV (0.2 M) and of BZ (0.4 M) are prepared in DMSO in order to prepare the various cell treatment media.

For the treatment, the culture medium is discarded and replaced with 1 ml of complete Ham's F10 medium supplemented with one of the molecules of interest at one of the following concentrations, 75 µM RSV, or 400 µM BZ, or 20 µM RSV, or 30 µM RSV, or 25 µM RSV, or 35 µM RSV, or the culture medium is discarded and replaced with 1 ml of complete Ham's F10 medium supplemented with a combination of the two molecules of interest at the following concentrations: (20 µM RSV+25 µM RSV), or (30 µM RSV+35 µM RSV). Additional wells receive 1 ml of complete medium supplemented with the diluent of the molecules of interest only (<0.05% DMSO). Each of these treatment conditions is applied in triplicate (3 wells) for each patient, in each experiment. The 24-well dishes are then incubated at 37° C. for 48 hours. Thus, the cells of each individual studied are treated in all of the conditions listed, in parallel, for 48 hours, before the measurement of palmitate β-oxidation.

Measurement of Palmitate β-Oxidation.

The fatty acid used is palmitate labeled with tritium at positions 9 and 10 ($^3$H-Pal). A stock solution is prepared beforehand by mixing 100 µl of $^3$H-Pal, 130 µl of 50 mM "cold" palmitate and 13 ml of 25 mg/ml BSA solution. A $^3$H-Pal/BSA (bovine serum albumin) complex ensuring good palmitate solubilization is thus obtained (final palmitate concentration: 500 µM).

The test of $^3$H-palmitate oxidation is carried out on fibroblasts seeded in a 24-well plate. The culture medium is first discarded and the wells are rinsed three times with PBS. A 125 µM $^3$H-Pal working solution is prepared, from the 500 µM stock solution, in PBS with Ca/Mg, supplemented with 1 mM carnitine. 200 µl of this $^3$H-Pal solution is introduced into each well and the plates are incubated at 37° C. for 2 hours.

During this time, three counting vials are prepared for the measurement of specific radioactivity (RDA, in CPM/nmol of fatty acids) of the reaction medium. These vials contain 5 ml of scintillation fluid, 1.5 ml of distilled water, and 20 µl of $^3$H-Pal/BSA solution. The scintillation fluid converts the radioactive energy of $^3$H into light energy, which thus makes it possible to measure radioactivity, expressed in counts per minute (CPM), using a liquid scintillation counter.

At the end of 2 hours of incubation, 200 µl is taken from each well and mixed with 200 µl of 10% trichloroacetic acid (TCA). This strong acid ensures the precipitation of unmetabolized BSA/AG complex. The tubes are then centrifuged at 3300 rpm for 10 minutes at 4° C.

After centrifugation, 350 µl of supernatant is taken and mixed with 55 µl of 6 M NaOH in order to neutralize the pH. The total volume, or 450 µl, is transferred to an ion-exchange resin column which retains the tritiated water. These columns are then transferred to scintillation vials. The tritiated water is then eluted with 1.7 ml of distilled water. 5 ml of scintillation fluid is added to the tritiated water and the vials are placed in the liquid scintillation counter.

Results

For the two patients suffering from moderate VLCAD deficiency, the results obtained are presented in Tables 1 and 2 below and in FIG. 1.

TABLE 1

% increase in fatty acid oxidation (FAO) observed for patient E3536

| E3536 | % increase in fatty acid oxidation (FAO) |
|---|---|
| 75 µM RSV alone | 145% |
| 400 µM BZ alone | 128% |

| E3536 | Condition 1 | | | Condition 2 | | |
|---|---|---|---|---|---|---|
| | | | % increase in fatty acid oxidation (FAO) | | | |
| RSV alone | 20 µM RSV | Measured | 81% | 30 µM RSV | Measured | 106% |
| BZ alone | 25 µM BZ | Measured | 7% | 35 µM BZ | Measured | 20% |
| Combination of BZ + RSV | 20 µM RSV + 25 µM BZ | Measured | 118% | 30 µM RSV + 35 µM BZ | Measured | 252% |
| | | Theoretical* | 88% | | Theoretical* | 126% |
| | | Synergy factor | ×1.34 | | Synergy factor | ×2 |

*Theoretical = sum of the percentages obtained with each compound used alone

TABLE 2

% increase in fatty acid oxidation (FAO) observed for patient CHA Ma

| CHA Ma | % increase in fatty acid oxidation (FAO) |
|---|---|
| 75 µM RSV alone | 67% |
| 400 µM BZ alone | 83% |

| CHA Ma | Condition 1 | | | Condition 2 | | |
|---|---|---|---|---|---|---|
| | | | % increase in fatty acid oxidation (FAO) | | | |
| RSV alone | 20 µM RSV | Measured | 22% | 30 µM RSV | Measured | 43% |
| BZ alone | 25 µM BZ | Measured | 1% | 35 µM BZ | Measured | 8% |
| Combination of BZ + RSV | 20 µM RSV + 25 µM BZ | Measured | 43% | 30 µM RSV + 35 µM BZ | Measured | 98% |
| | | Theoretical* | 23% | | Theoretical* | 51% |
| | | Synergy factor | ×1.87 | | Synergy factor | ×1.92 |

*Theoretical = sum of the percentages obtained with each compound used alone

Figure 1:
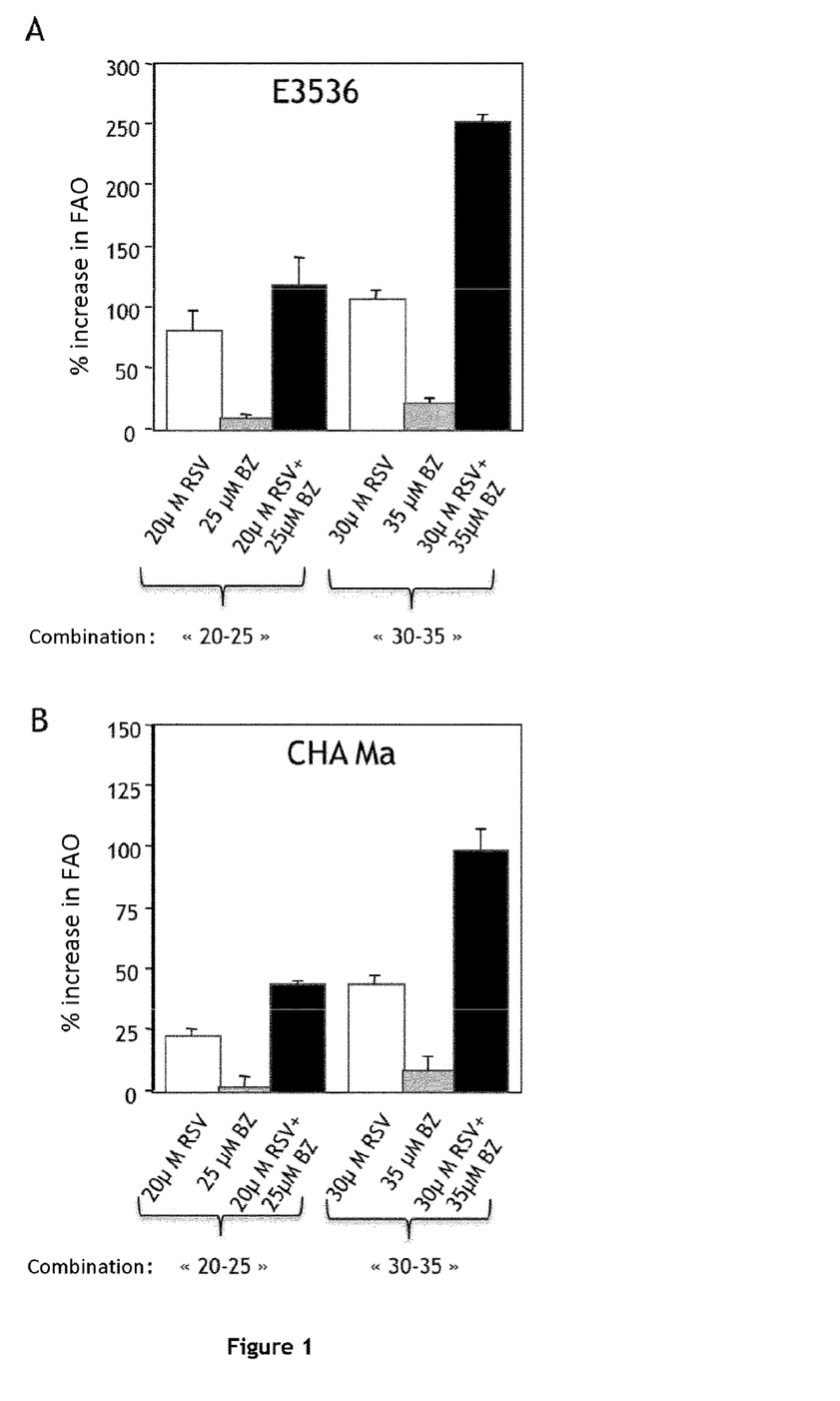
FIG. 1. Synergistic effect of resveratrol and bezafibrate for correcting VLCAD deficiencies in two patients (E3536 (A) and CHA Ma (B)). The percent increase in fatty acid oxidation (FAO) of each composition tested, compared to cells receiving carrier alone, is shown according to the composition tested.

Tables 1 and 2 and FIG. 1 show synergy between the effects of RSV and BZ, with a synergy factor of between 1.3 and 2, indicating that:
- the observed effect of the combination RSV+BZ is up to 2 times superior to the additive effect of each compound,
- synergy is particularly apparent in the BZ example, since the effects of 25 μM or 35 μM BZ alone are negligible (≤8%) or very weak (maximum 20%),
- the combination (30 μM RSV+35 μM BZ) shows effects superior or equal to those observed with 75 μM RSV alone or 400 μM BZ alone,
- more powerful effects are thus obtained with doses of these compounds much lower than if they had been used alone.

For the two patients suffering from moderate CPT2 deficiency, the results obtained are presented in Tables 3 and 4 below and in FIG. 2.

TABLE 3

% increase in fatty acid oxidation (FAO) observed for patient BRA Ma

| BRA Ma | % increase in fatty acid oxidation (FAO) |
|---|---|
| 75 μM RSV alone | 100% |
| 400 μM BZ alone | 88% |

% increase in fatty acid oxidation (FAO)

| BRA Ma | | Condition 1 | | | Condition 2 | |
|---|---|---|---|---|---|---|
| RSV alone | 20 μM RSV | Measured | 39% | 30 μM RSV | Measured | 48% |
| BZ alone | 25 μM BZ | Measured | 0% | 35 μM BZ | Measured | 6% |
| Combination of BZ + RSV | 20 μM RSV + 25 μM BZ | Measured | 53% | 30 μM RSV + 35 μM BZ | Measured | 118% |
| | | Theoretical* | 39% | | Theoretical* | 54% |
| | | Synergy factor | ×1.36 | | Synergy factor | ×2.18 |

*Theoretical = sum of the percentages obtained with each compound used alone

TABLE 4

% increase in fatty acid oxidation (FAO) observed for patient DIA Ke

| DIA Ke | % increase in fatty acid oxidation (FAO) |
|---|---|
| 75 μM RSV alone | 44% |
| 400 μM BZ alone | 62% |

% increase in fatty acid oxidation (FAO)

| DIA Ke | | Condition 1 | | | Condition 2 | |
|---|---|---|---|---|---|---|
| RSV alone | 20 μM RSV | Measured | 49% | 30 μM RSV | Measured | 66% |
| BZ alone | 25 μM BZ | Measured | 0% | 35 μM BZ | Measured | 6% |
| Combination of BZ + RSV | 20 μM RSV + 25 μM BZ | Measured | 70% | 30 μM RSV + 35 μM BZ | Measured | 119% |
| | | Theoretical* | 49% | | Theoretical* | 72% |
| | | Synergy factor | ×1.43 | | Synergy factor | ×1.65 |

*Theoretical = sum of the percentages obtained with each compound used alone

Figure 2:
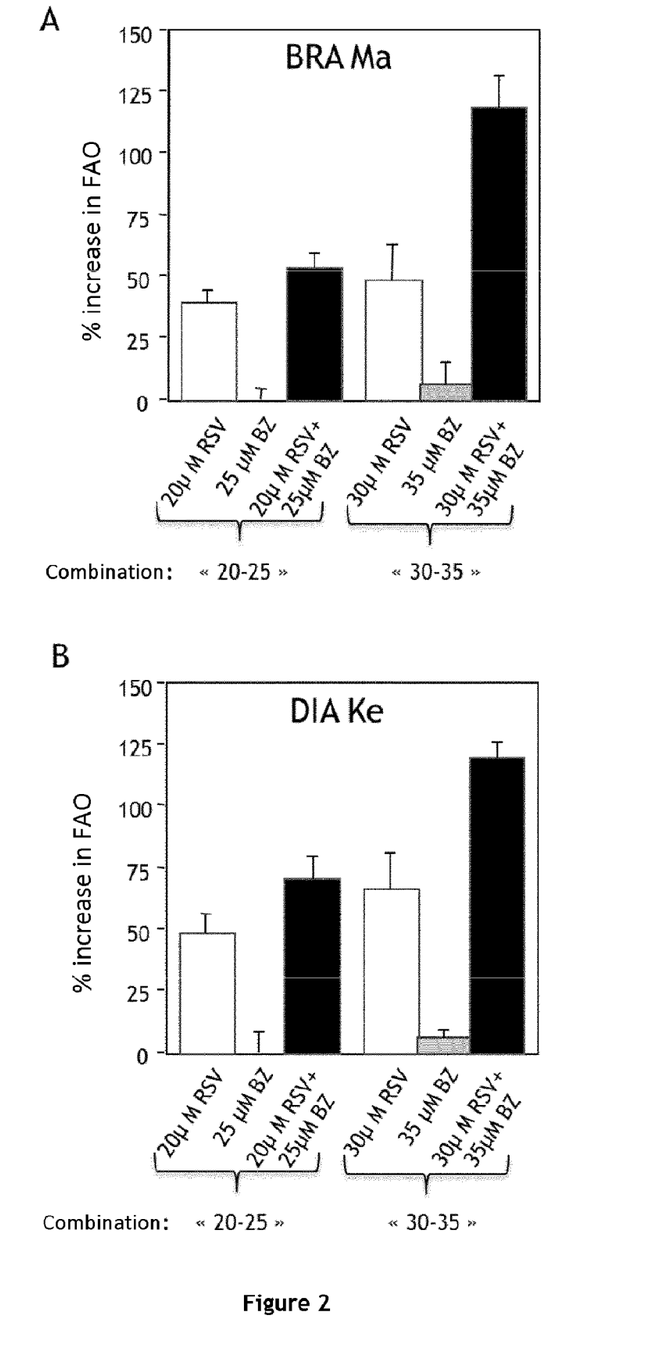
FIG. 2. Synergistic effect of resveratrol and bezafibrate for correcting CPT2 deficiencies in two patients (BRA Ma (A) and DIA Ke (B)). The percent increase in fatty acid oxidation (FAO) of each composition tested, compared to cells receiving carrier alone, is shown according to the composition tested.

Tables 3 and 4 and FIG. 2 show synergy between the effects of RSV and BZ, with a synergy factor of between 1.3 and 2, indicating that:
- the observed effect of the combination RSV+BZ is up to 2.2 times superior to the additive effect of each compound,
- synergy is particularly apparent in the BZ example, since the effects of 25 μM or 35 μM BZ alone are negligible (0 to 6%),
- the combination (30 μM RSV+35 μM BZ) shows effects superior or equal to those observed with 75 μM RSV alone or 400 μM BZ alone,
- more powerful effects are thus obtained with doses of these compounds much lower than if they had been used alone.

The same conclusions regarding the existence of a synergistic effect between BZ and RSV, making it possible to decrease the dose of BZ to a level not producing a significant effect when BZ is used alone, are thus applicable to both patients suffering from moderate VLCAD deficiency and patients suffering from moderate CPT2 activity.

In both cases, a correction of the deficiencies is obtained in vitro by using the combination 30 μM RSV+35 μM BZ, which corresponds to a reduction in dose by a factor of 2.5 for RSV (resveratrol alone corrects the deficiency only at 75 μM) and by a factor of 11.4 for BZ (BZ alone corrects the deficiency only at 400 μM).

Figure 3:
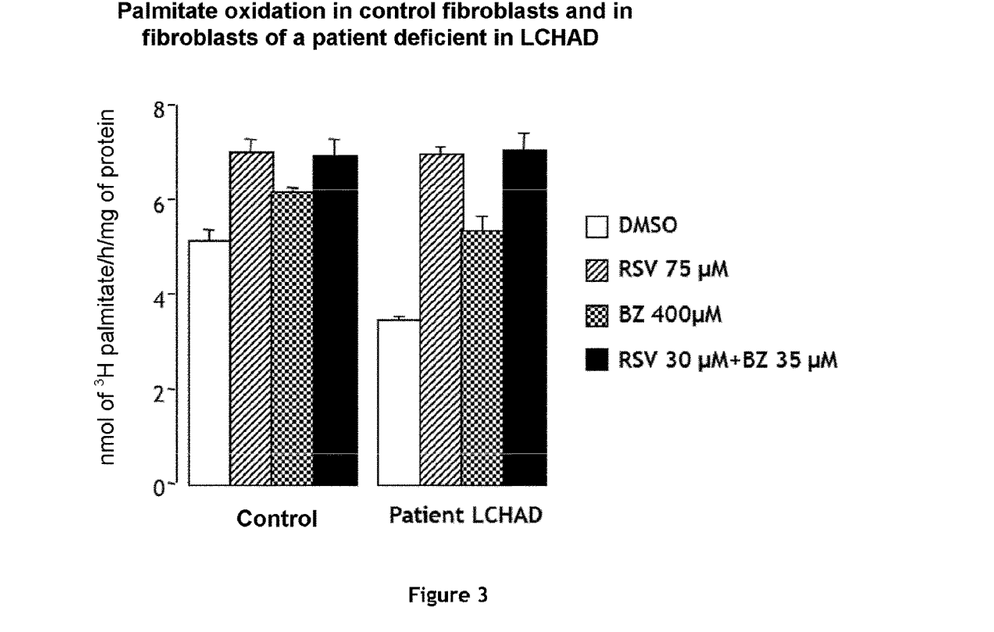
FIG. 3. Palmitate oxidation in fibroblasts of controls and of a patient deficient in LCHAD. The amount of tritiated palmitate oxidized per hour and per mg of protein in cells of a healthy control subject ("Control") and in cells of a patient deficient in LCHAD ("Patient LCHAD") is shown for cells grown in the presence of DMSO (carrier), 75 µM RSV, 400 µM BZ, or (30 µM RSV+35 µM BZ).

Additional results concerning a patient suffering from deficiency in LCHAD, a third enzyme involved in β-oxidation, are presented in FIG. 3. The results show that the combination of molecules (RSV+BZ) at low dose (30 μM RSV+35 μM BZ) is as effective as RSV alone, at an optimal dose of 75 μM (a dose however more than two times higher than that used in the combination), and more effective than BZ alone, at an optimal dose of 400 μM (a dose however more than 10 times higher than that used in the combination).

Conclusions

The combination (BZ+RSV) at low doses (20 µM RSV+ 25 µM BZ, or 30 µM RSV+35 µM BZ) thus showed its efficacy for correcting three types of moderate deficiencies of enzymes involved in β-oxidation, with efficacy similar to that obtained with much higher doses of each product alone. Indeed, the fact of combining the two molecules makes it possible to decrease by a factor of 2 the dose of RSV and by a factor of 10 the dose of BZ needed to correct the deficiency. This performance is made possible by the existence of unexpected synergistic effects between BZ and RSV. These results support the general applicability of the combined use of BZ and RSV for treating or preventing moderate β-oxidation deficiencies.

Example 2: Effect of Low Doses of Resveratrol (RSV) (30 µM) in Combination with Low Doses of Bezafibrate (BZ) (35 µM) in Fibroblasts of Patients Suffering from Moderate Respiratory Chain Deficiency The effects of low doses of resveratrol (RSV) (30 µM) in combination with low doses of bezafibrate (BZ) (35 µM) were also tested in fibroblasts of patients suffering from moderate respiratory chain deficiency.

Patient and Methods

Patient

Patient deficient in complex IV:

TUFRu: Mutation of the COX10 gene (genotype Y270C/P382Q). Oxygen uptake value measured in the absence of treatment: 4.0±0.5 OUR/$10^6$ cells (versus 7.2±0.8 OUR/$10^6$ cells in the control) or −44%.

Treatments Applied

The fibroblasts are grown at 37° C. in complete RPMI 1640 medium, i.e., supplemented with 10% FCS, 100 U/ml penicillin and 0.1 mg/ml streptomycin and 5 µg/ml Plasmocin™ (Invivogen) in T75 culture flasks until about 75% confluence is obtained. The day of treatment, stock solutions of RSV (0.2 M) and of BZ (0.4 M) are prepared in DMSO. The culture medium is discarded and replaced with an identical volume of complete RPMI medium supplemented with one of the molecules of interest at one of the following concentrations, 75 µM RSV, or 400 µM BZ, or the culture medium is discarded and replaced with an identical volume of complete RPMI medium supplemented with a combination of the two molecules of interest at the following concentrations: (30 µM RSV+35 µM RSV). For each individual, a T75 of cells is also treated with complete RPMI medium supplemented only with the diluent of the molecules of interest (<0.05% DMSO). Each of these treatment conditions is applied for each patient, in each experiment. The flasks are then incubated at 37° C. for 48 hours. Thus, the cells of each individual studied are treated in all of the conditions listed, in parallel, for 48 hours, before the measurement of oxygen uptake.

Measurement of Cellular Oxygen Uptake: Oxoplate®

Principle

The Oxoplate® OP96U is a 96-well plate, each well containing at its bottom a thin polymer in which two different fluorescent probes, a so-called "indicator" probe and a so-called "reference" probe, are integrated. The fluorescence intensity of the indicator probe ($I_{indicator}$) depends on the oxygen content of the sample. The fluorescence intensity of the reference probe ($I_{reference}$) is oxygen-insensitive. The intensities emitted by these two probes are measured with a plate reader (Infinite M200, Tecan) and at each measurement point an $I_R$ ratio ($I_{indicator}/I_{reference}$) is calculated The fluorescence of the indicator probe is quenched by the presence of oxygen. Thus, the higher the quantity of oxygen in the medium, the lower the fluorescence intensity of the indicator probe. And thus, the cells' oxygen uptake will be reflected in an increase in the fluorescence of the indicator probe.

For each experiment, with the aim of calibrating the measurements, two additional wells are included: a well corresponding to 0% oxygen (volume of water depleted of $O_2$ by a powerful reducing agent, dithionite), a well corresponding to 100% oxygen (vigorously shaken volume of water). For each of these two wells, the average of the $I_R$ ratios obtained throughout the kinetics is determined. These values, called $k_0$ and $k_{100}$, can then be used to estimate, in the wells containing the cell suspensions, percent oxygen saturation ($PO_2$) over time, using the following formula:

$$pO_2 = 100\left(\frac{k_0}{I_R} - 1\right) \Big/ \left(\frac{k_0}{k_{100}} - 1\right)$$

The oxygen uptake rate (OUR) values thus correspond to the values of the maximum slopes of the $PO_2$ reduction kinetics.

Method

For measuring oxygen uptake, all the wells are first seeded with the same quantity of suspended cells. Thus, after treatment, the various cell cultures are trypsinized and counted using a cell counter (CASY TT). They are then centrifuged and taken up in a variable volume of RPMI 1640 without glucose (LifeTechnologies) so as to obtain a cell suspension of 18,000 cells/µl for the controls and 20,000 cells/µl for the patients. Aliquots of each cell suspension (3×3 µl) are taken for the protein assay. Next, 10 µl of cell suspension is deposited at the bottom of each Oxoplate® well (minimum of 3 wells per test condition), and then a volume of 100 µl of RPMI 1640 without glucose containing 1.25 µM CCCP is added. These cell suspensions are then covered with 200 µl of heavy mineral oil (Sigma) preheated to 37° C. The mineral oil ensures the "air-tightness" of the measurement by preventing any exchange of air between the cell suspensions and the ambient air. The fluorescences emitted by the probes are read from the bottom of the wells, every 30 seconds for 1 hour, using an Infinite® M200 µlate reader (Tecan, Magellan software) preheated to 37° C. The excitation wavelength (540 nm) is the same for the indicator probe and the reference probe, which will emit at 650 nm and 590 nm, respectively.

The fluorescence intensity kinetics were analyzed using the Microsoft Excel software.

Results

Figure 4:
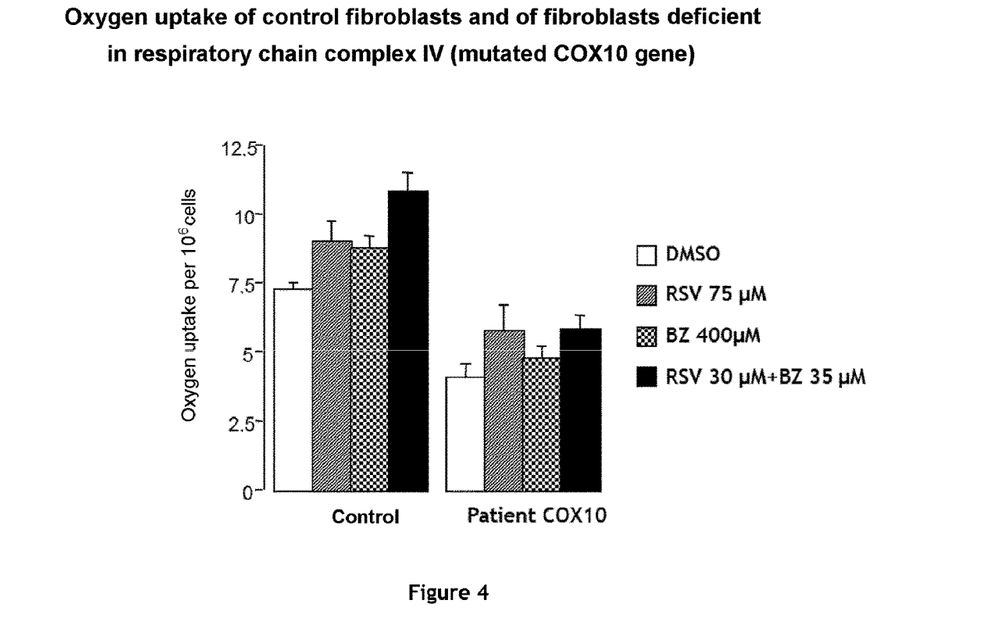
FIG. 4. Oxygen uptake of control fibroblasts and fibroblasts deficient in respiratory chain complex IV (mutated COX10 gene). Oxygen uptake per million cells is shown in cells of a healthy control subject ("Control") and in cells of a patient deficient in respiratory chain complex IV ("Patient COX10") for cells grown in the presence of DMSO (carrier), 75 µM RSV, 400 µM BZ, or (30 µM RSV+35 µM BZ).

The results obtained are presented in FIG. 4.

This shows that the combination (30 µM RSV+35 µM BZ) is as effective as RSV alone, at an optimal dose of 75 µM (a dose however more than two times higher than that used in the combination), and more effective than BZ alone, at an optimal dose of 400 µM (a dose however more than 10 times higher than that used in the combination).

Conclusions

These results show that the combination of molecules (RSV+BZ) is also effective at low doses for improving the respiratory capacities of fibroblasts of a patient deficient in respiratory chain complex IV, thus supporting the use of this combination at low dose for the prevention and treatment of moderate respiratory chain deficiencies.

BIBLIOGRAPHIC REFERENCES

Aires V, Delmas D, Le Bachelier C, Latruffe N, Schlemmer D, Benoist J F, Djouadi F, Bastin J. Stilbenes and resveratrol metabolites improve mitochondrial fatty acid oxidation defects in human fibroblasts. Orphanet J Rare Dis. 2014 Jun. 5; 9:79.

Andreux P A, Houtkooper R H, Auwerx J. Pharmacological approaches to restore mitochondrial function. Nat Rev Drug Discov. 2013 June; 12(6):465-83.

Bastin J, Aubey F, Rötig A, Munnich A, and Djouadi F. Activation of Peroxisome Proliferator-Activated Receptor Pathway Stimulates the Mitochondrial Respiratory Chain and Can Correct Deficiencies in Patients' Cells Lacking Its Components. J Clin Endocrinol Metab, 2008, 93:1433-1441.

Bastin J, Lopes-Costa A, and Djouadi F. Exposure to resveratrol triggers pharmacological correction of fatty acid utilization in human fatty acid oxidation-deficient fibroblasts. Hum. Mol Genet. 2011, 20:2048-2057.

Bhatt, J. K., Thomas, S. Et Nanjan, M. J. Resveratrol supplementation improves glycemic control in type 2 diabetes mellitus. Nutr. Res. 32, 537-541 (2012).

Bonnefont J P*, Bastin J* (*equal contribution), Laforét P, Aubey F, Mogenet A, Romano S, D Ricquier, Gobin-Limballe S, Vassault A, Behin A, Eymard B, Bresson J L, and Djouadi F. Long term follow-up of bezafibrate treatment in the myopathic form of Carnitine-PalmitoylTransferase 2 deficiency. Clin Pharmacol Ther, 2010, 88:101-108.

Bonnefont J P, Bastin J, Behin A, and Djouadi F. Bezafibrate for an Inborn Mitochondrial Beta-Oxidation Defect. N Engl J Med, 2009 360; 8.

Chaturvedi R K, Beal M F. Mitochondria targeted therapeutic approaches in Parkinson's and Huntington's diseases. Mol Cell Neurosci. 2013 July; 55:101-14.

Chaturvedi R K, Flint Beal M. Mitochondrial diseases of the brain. Free Radic Biol Med. 2013 October; 63:1-29.

Djouadi, Aubey F, Schlemmer D, Ruiter J P, Wanders R J, Strauss A W and Bastin J. Bezafibrate increases Very Long Chain AcylCoA Dehydrogenase protein and mRNA expression in deficient fibroblasts, and is a potential therapy for fatty acid oxidation disorders. Hum Mol Genet, 2005, 14:2695-2703.

Djouadi F, Aubey F, Schlemmer D and Bastin J. Peroxisome Proliferator Activated Receptor delta (PPARd) agonist but not PPARalpha corrects Carnitine Palmitoyl Transferase 2 (CPT2) deficiency in human muscle cells. J. Clin. Endocrinol. Metab, 2005, 90:1791-1797.

Djouadi F, Bonnefont J P, Thuillier L, Droin V, Khadom N, Munnich A, and Bastin J. Correction of fatty acid oxidation in carnitine palmitoyl transferase 2-deficient cultured skin fibroblasts by bezafibrate. Pediatr Res, 2003, 54:446-51.

Eaton S, Bartlett K, Pourfarzam M. Mammalian mitochondrial beta-oxidation. Biochem J. 1996 Dec. 1; 320 (Pt 2):345-57.

Johri, A., Calingasan, N. Y., Hennessey, T. M., Sharma, A., Yang, L., Wille, E., Chandra, A., Beal, M. F., 2012. Pharmacologic activation of mitochondrial biogenesis exerts widespread beneficial effects in a transgenic mouse model of Huntington's disease. Hum. Mol. Genet. 21, 1124-1137.

Kompare M, Rizzo W B. Mitochondrial fatty-acid oxidation disorders. Semin Pediatr Neurol. 2008 September; 15(3): 140-9.

Lagouge, M., Argmann, C., Gerhart-Hines, Z., Meziane, H., Lerin, C., Daussin, F., Messadeq, N., Milne, J., Lambert, P., Elliott, P., Geny, B., Laakso, M., Puigserver, P., Auwerx, J., 2006. Resveratrol improves mitochondrial function and protects against metabolic disease by activating SIRT1 and PGC-1alpha. Cell 127, 1109-1122.

Papa S, De Rasmo D. Complex I deficiencies in neurological disorders. Trends Mol Med. 2013 January; 19(1):61-9.

Patti, M. E., Corvera, S. The role of mitochondria in the pathogenesis of Type 2 Diabetes. Endocrine Reviews, 2010, 31:364-395.

Rötig A, Munnich A. Genetic features of mitochondrial respiratory chain disorders. J Am Soc Nephrol. 2003 December; 14(12):2995-3007.

Timmers S, Konings E, Bilet L, Houtkooper R H, van de Weijer T, Goossens G H, Hoeks J, van der Krieken S, Ryu D, Kersten S, Moonen-Kornips E, Hesselink M K, Kunz I, Schrauwen-Hinderling V B, Blaak E E, Auwerx J, Schrauwen P. Calorie restriction-like effects of 30 days of resveratrol supplementation on energy metabolism and metabolic profile in obese humans. Cell Metab. 2011 Nov. 2; 14(5):612-22.

Vafai, S. B., Mootha, V. K. Mitochondrial disorders as windows into an ancient organelle. 2012, Nature, 491: 374-383.

The invention claimed is:

1. A method of therapeutic treatment of a disease involving mitochondrial energy dysfunction in a patient in need thereof, comprising administering to said patient effective amounts in combination 1) of bezafibrate and 2) of resveratrol, cis-resveratrol, dihydro-resveratrol, piceid or mixtures thereof, wherein said disease involving mitochondrial energy dysfunction is characterized by moderate deficiency in mitochondrial long-chain fatty acid β-oxidation due to the presence of at least one mutation on each allele of one of the genes encoding one of the following enzymes: CPT2, VLCAD, and LCHAD.

2. The method according to claim 1, wherein the combination 1) of bezafibrate and 2) of resveratrol, cis-resveratrol, dihydro-resveratrol, piceid or mixtures thereof is administered to a subject whose cells have palmitate β-oxidation activity of at least 30% of the activity of this same process in healthy control cells.

3. The method according to claim 1, wherein the moderate deficiency in mitochondrial long-chain fatty acid β-oxidation is due to the presence of at least one mutation on each allele of the gene encoding CPT2.

4. The method according to claim 1, wherein the treated subject suffers from moderate deficiency in mitochondrial long-chain fatty acid β-oxidation due to the presence of at least one mutation on each allele of the gene encoding VLCAD.

5. The method according to claim 1, wherein the patient is selected from those for whom the combined presence 1) of bezafibrate and 2) of resveratrol, cis-resveratrol, dihydro-resveratrol, piceid or mixtures thereof improves β-oxidation in the patient's cells in vitro.

6. The method according to claim 1, wherein a combination 1) of bezafibrate and 2) of resveratrol is used.

* * * * *

UNITED STATES PATENT AND TRADEMARK OFFICE
CERTIFICATE OF CORRECTION

PATENT NO. : 10,376,484 B2
APPLICATION NO. : 15/105116
DATED : August 13, 2019
INVENTOR(S) : Jean Bastin et al.

Page 1 of 1

It is certified that error appears in the above-identified patent and that said Letters Patent is hereby corrected as shown below:

In the Specification

Column 5, Lines 15-25 should read:
By "*cis*–resveratrol" or "*cis*–RSV" is meant 5–[(Z)–2–(4–hydroxyphenyl)–ethenyl]benzene–1,3–diol (CAS no. 61434–67–1) of formula (III) below:

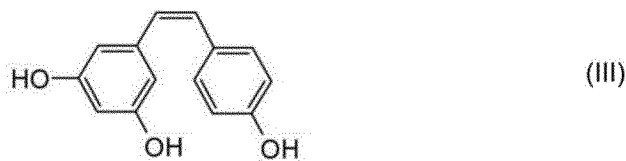

Signed and Sealed this
Twenty-eighth Day of January, 2020

Andrei Iancu
*Director of the United States Patent and Trademark Office*